(12) United States Patent
Daniel

(10) Patent No.: US 10,064,795 B2
(45) Date of Patent: Sep. 4, 2018

(54) ATOMIZING SPRAY FOR GRIP ENHANCEMENT

(71) Applicant: Grip Tight Sport LLC, Louisville, KY (US)

(72) Inventor: Christopher Michael Daniel, Louisville, KY (US)

(73) Assignee: Grip Tight Sport LLC, Louisville, KY (US)

( * ) Notice: Subject to any disclaimer, the term of this patent is extended or adjusted under 35 U.S.C. 154(b) by 0 days.

(21) Appl. No.: 15/160,193

(22) Filed: May 20, 2016

(65) Prior Publication Data

US 2016/0338917 A1 Nov. 24, 2016

Related U.S. Application Data

(60) Provisional application No. 62/165,196, filed on May 22, 2015.

(51) Int. Cl.
| | |
|---|---|
| A61K 8/19 | (2006.01) |
| A61K 8/02 | (2006.01) |
| A61K 8/34 | (2006.01) |
| A61K 8/25 | (2006.01) |
| A61Q 15/00 | (2006.01) |
| B65D 83/06 | (2006.01) |
| B65D 83/64 | (2006.01) |
| B65D 83/00 | (2006.01) |
| B65D 83/62 | (2006.01) |
| B65D 83/48 | (2006.01) |
| B65D 83/14 | (2006.01) |
| B05B 11/00 | (2006.01) |

(52) U.S. Cl.
CPC ............. *A61K 8/19* (2013.01); *A61K 8/0241* (2013.01); *A61K 8/25* (2013.01); *A61K 8/34* (2013.01); *A61Q 15/00* (2013.01); *B05B 11/3047* (2013.01); *B05B 11/3057* (2013.01); *B65D 83/0061* (2013.01); *B65D 83/06* (2013.01); *B65D 83/62* (2013.01); *B65D 83/64* (2013.01); *B65D 83/752* (2013.01); *A61K 2800/20* (2013.01); *B05B 11/30* (2013.01); *B65D 83/48* (2013.01)

(58) Field of Classification Search
CPC .... A45D 33/02; A45D 34/00; A61K 2800/20; A61K 8/0241; A61K 8/19; A61K 8/25; A61K 8/34; A61Q 15/00; B65D 83/06; B65D 83/202; B65D 83/207; B65D 83/32; B65D 83/64
See application file for complete search history.

(56) References Cited

U.S. PATENT DOCUMENTS

| | | | |
|---|---|---|---|
| 1,163,475 A | 12/1915 | Silbermann | |
| 2,765,212 A | 6/1961 | Froelich | |
| 2,987,447 A * | 6/1961 | Ward | A61K 8/19 106/36 |
| 3,788,521 A | 1/1974 | Laauwe | |
| 4,001,391 A | 1/1977 | Feinstone et al. | |
| 4,134,523 A | 1/1979 | Hansen et al. | |
| RE30,093 E | 9/1979 | Burger | |
| 4,187,985 A | 2/1980 | Goth | |
| 4,239,407 A | 12/1980 | Knight | |
| 4,495,168 A | 1/1985 | Schmolka | |
| 4,510,734 A | 4/1985 | Banks et al. | |
| 4,572,690 A | 2/1986 | Savanuck | |
| 5,204,088 A * | 4/1993 | Noebel | A61K 8/046 424/401 |
| 5,249,747 A | 10/1993 | Hanson et al. | |
| 5,364,464 A | 11/1994 | Sereboff | |
| 5,417,961 A | 5/1995 | Nearn et al. | |
| 5,565,023 A | 10/1996 | Sereboff | |
| 5,639,025 A | 6/1997 | Bush | |
| 5,788,389 A | 8/1998 | de Laforcade | |
| 5,881,925 A | 3/1999 | Ando | |
| 5,886,089 A | 3/1999 | Knowlton | |
| 6,627,178 B1 | 9/2003 | Cawthon | |
| 6,656,257 B2 | 12/2003 | Cohen | |
| 7,431,918 B2 | 10/2008 | Shelley et al. | |
| 9,717,679 B1 | 8/2017 | Cawthon | |
| 2005/0079229 A1 | 4/2005 | Cawthon | |
| 2006/0159640 A1 | 7/2006 | Plunk | |
| 2010/0015189 A1* | 1/2010 | Perron | A61K 8/044 424/401 |
| 2011/0095103 A1* | 4/2011 | Schiemann | A61K 8/046 239/589 |
| 2015/0139917 A1* | 5/2015 | Gawtrey | A61Q 5/02 424/46 |
| 2016/0331863 A1 | 11/2016 | Cawthon | |

OTHER PUBLICATIONS

Sportsman's Guide; 2-oz Pro Grip product description page; obtained from: <https://www.sportsmansguide.com/product/index/2-oz-pro-grip?a=55660>, Printed May 2018.

IPSCStore; Progrip Lotion (60ML) product description page; obtained from: <https://www.ipscstore.com/en/handgrips/331-18-100254-progrip-lotion-60-ml-2000000003313.html>, Printed May 2018.

Username: Build4u; "Slippery Hands!", Brian Enos's Forums . . . Maku mozo!; Comment dated Dec. 26, 2014; Michigan; obtained from: <https://forums.brianenos.com/topic/169312-slippery-hands/? page=2>.

Username: Build4u; "Hand chalk/grip lotions"; Brian Enos's Forums . . . Maku mozo!; Comment dated May 20, 2016; Michigan; obtained from: <https://forums.brianenos.com/topic/227095-hand-chalkgrip-lotions/?page=3>.

\* cited by examiner

*Primary Examiner* — Mark V Stevens

(74) *Attorney, Agent, or Firm* — Taft Stettinius & Hollister LLP; Gregory B. Coy

(57) ABSTRACT

Provided by the invention are systems for applying antiperspirant grip enhancement compositions to a selected skin treatment area. Application of the antiperspirant grip enhancement composition is accomplished by forming the composition into a mist or spray using an atomizing spray dispenser.

19 Claims, 6 Drawing Sheets

ATOMIZING SPRAY FOR GRIP ENHANCEMENT

CROSS-REFERENCE TO RELATED APPLICATION

This application claims the benefit of U.S. Provisional Application No. 62/165,196, filed May 22, 2015

BACKGROUND

1. Field of the Invention

The present invention relates to methods, compositions and systems for the enhancement of grip between skin and tools, particularly sports equipment. The present invention is in the technical field of grip enhancement. More particularly, the present invention is in the technical field of antiperspirant grip enhancement spray for sporting activities.

2. Discussion of Related Art

The gripping portion of sporting equipment is generally made of materials that may become difficult to grasp when wet, particularly due to perspiration. Therefore, controlling perspiration of the hands is critical in many sporting activities. Slippage of grip due to perspiration is a problem in any sporting event that requires the tight grip of an implement or apparatus. This slippage negatively impacts sports performance and in some sports poses a severe threat to safety. In an attempt to control perspiration and improve grip, various materials that can be applied to the skin or sports implement have been developed. Conventional methods of improving grip have been aimed toward direct application of absorptive antiperspirant powders.

Gym chalk is commonly used as an antiperspirant grip enhancer for athletic activities such as powerlifting, weightlifting, gymnastics, track and field, Crossfit, and rock climbing. When rubbed on the skin, this compound forms a thin layer that acts as an antiperspirant with the intention of absorbing sweat. Perspiration causes a severe threat to safety in sports such as weightlifting, pole vaulting, Crossfit, and gymnastics. In these sports, a loss of grip on the sports implement or apparatus can be particularly dangerous for the athlete. Moreover, slippage of grip equates to a loss of energy that can negatively affect performance. Common compounds typically include magnesium carbonate as discussed in U.S. Pat. No. 1,163,475 to Silbermann and U.S. Pat. No. 2,765,212 to Froelich. Other compositions for grip enhancement include talc as described in U.S. Pat. No. 2,987,447 to Ward.

Some athletes use rosin in the form of a rosin bag as described in U.S. Pat. No. 4,572,690 to Savanuck or rosin powder to apply a light application to their hands or implement to improve grip. A rosin bag is a traditional piece of equipment generally being used both by a pitcher and a hitter in baseball to make more certain of their grip on the ball and the bat, respectively. Similarly, tennis and golf players can require a light application of powdered rosin to their hands to aid in making their grips more certain U.S. Pat. No. 5,565,023 to Sereboff and U.S. Pat. No. 5,364,464 to Sereboff discusses grip enhancing compositions that comprise inorganic powder such as magnesium carbonate or calcium carbonate or magnesium silicate or aluminum chloride. Examples of other patents that describe various grip enhancing compositions include the following: U.S. Pat. No. 6,656,257 to Cohen, U.S. Pat. No. 7,431,918 to Shelley et al., U.S. Pat. No. 5,886,089 to Knowlton, U.S. Pub. No. 2006159640 to Plunk.

Delivery mechanisms for various compositions as atomized sprays are discussed in U.S. Pub. No. 20050079229 to Cawthon. These, and all other references cited herein are hereby incorporated by reference herein in their entireties.

The fundamental disadvantages of the grip enhancement solutions known in the art however, are their lack of staying power, permanence, and relatively poor effectiveness. Major drawbacks on most grip enhancing products currently available for sport use is that they are messy to administer to the skin or sports implement and inefficient due to spillage and overuse. Such products require that the user applying the product spread the product by rubbing the same onto the skin or implement either from a block of compound or a crushed powder form of compound. Most currently available products are inefficient in transportation and application due to spillage of powdered forms and breakage of block forms of compounds. Because of the powdery nature of most currently available products, they inadequately cover the fine crevices of the skin. This leads to inefficiencies due to overuse in a single application with users attempting to completely cover the desired surface including fine crevices. Currently available products are typically extremely dry and thus adhere poorly to surfaces. Perspiration on the skin, for example, can easily dislodge the compounds, which subsequently leads to inefficiencies in use due to the need for frequent reapplication. Additionally, most grip enhancement products available are only available in the color white which sometimes makes it difficult to see which areas of the skin have been covered and exactly where the implement was gripped.

The above shortcomings of the prior art are addressed by the present invention, which provides methods, compositions, and systems for administering grip enhancers for sport use without the mess, inconvenience, and inefficiencies experienced in the prior art.

SUMMARY OF THE INVENTION

The present invention addresses a number of problems associated with currently known grip enhancement products by providing methods, compositions, and systems for grip enhancement involving application of a composition as an atomized spray. Provided by the invention are systems for applying a variety of grip enhancement compounds to improve gripping of tools or implements. These delivery mechanisms allow easier transportation of compounds and more efficient use of compounds.

Although particular embodiments of the present invention have been described in the foregoing description, it is to be understood that the present invention is not to be limited to just the embodiments disclosed, but that they are capable of numerous rearrangements, modifications and substitutions without departing from the description herein.

It is an object of the invention to provide novel methods, compositions and systems for enhancement of grip between skin and sports implements or tools.

It is another object of the invention to provide novel methods, compositions and systems for enhancement of grip whereby a composition may be administered to a skin surface by atomizing the composition and propelling the atomized composition toward the skin surface.

Further objects, advantages, and features of the present invention will be apparent from the detailed description herein.

BRIEF DESCRIPTION OF THE DRAWINGS

Although the characteristic features of this invention will be particularly pointed out in the claims, the invention itself, and the manner in which it may be made and used, may be better understood by referring to the following description taken in connection with the accompanying figures forming a part hereof.

DETAILED DESCRIPTION OF THE PREFERRED EMBODIMENTS

For purposes of promoting an understanding of the principles of the invention, reference will now be made to particular embodiments of the invention and specific language will be used to describe the same. It will nevertheless be understood that no limitation of the scope of the invention is thereby intended, such alterations and further modifications in the invention, and such further applications of the principles of the invention as described herein being contemplated as would normally occur to one skilled in the art to which the invention pertains.

Figure 6:
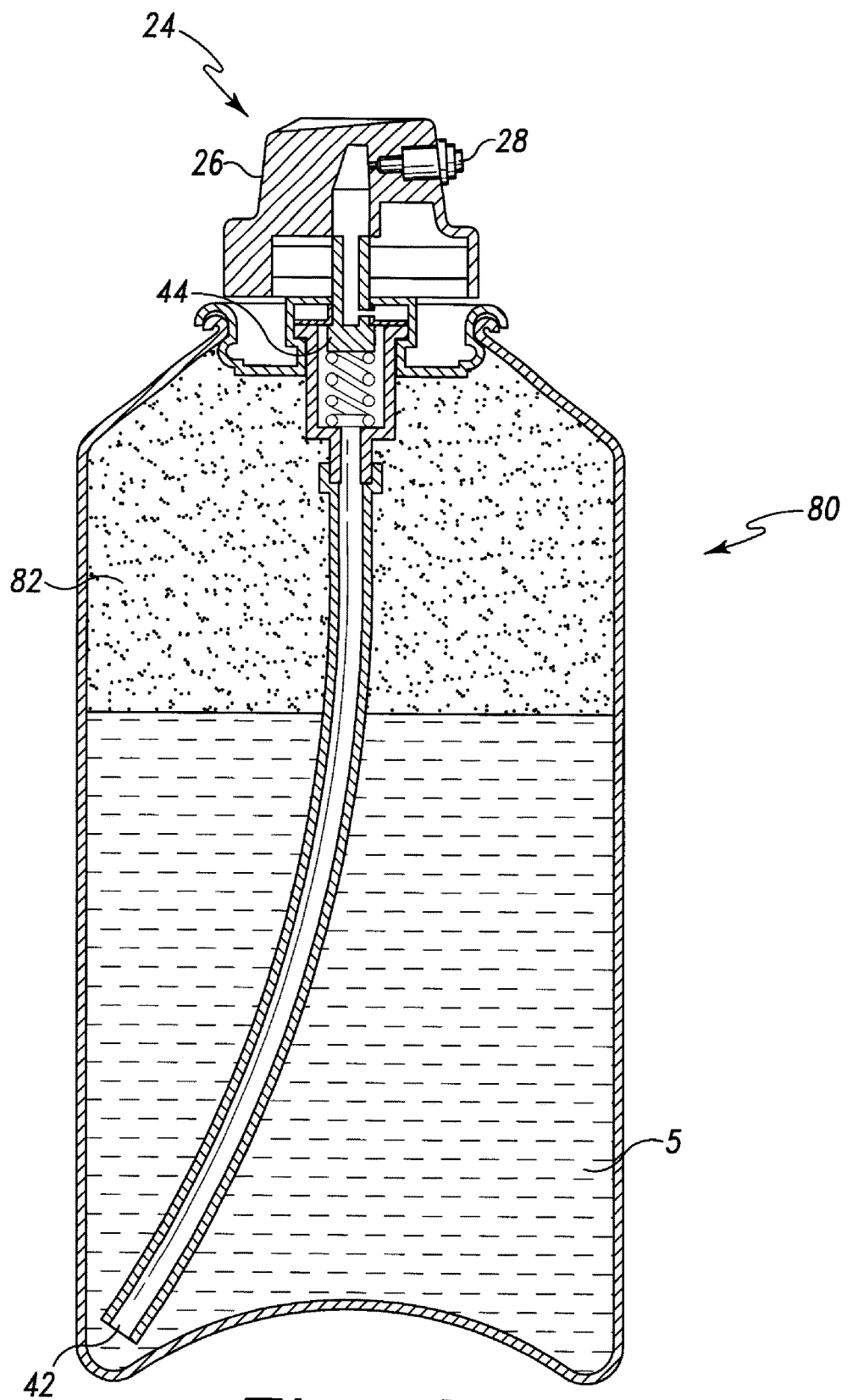
FIG. 6 is a sectional side elevational view of a representative aerosol dispenser in accordance with another embodiment of the invention.

Referring to FIG. 6, to practice the invention, a grip enhancement composition 5 is placed into an atomizing spray dispenser 80. The dispenser is preferably a container equipped with a spray delivery mechanism 24 configured to atomize and propel the composition toward a treatment surface by entraining the same in a carrier stream comprising an inert pressurized propellant gas 82. Examples of common propellants used include liquefied petroleum gas, chlorofluorohydrocarbons, butanes, propanes, carbon dioxide, nitrous oxide, nitrogen, dimethyl ether, heptane, and isopropanol. Other propellants may be used. It will nevertheless be understood that no limitation of the type of propellant is thereby intended. When such a device is actuated, the composition is released from the container, entrained in a gaseous stream, atomized, and propelled substantially in a predetermined direction by using energy provided by the pressurized gas. Compositions described herein exhibit excellent features for the enhancement of grip. When a proper amount of the composition is atomized and propelled by a suitable atomizing spray delivery mechanism, the composition forms a thin, fast-drying, antiperspirant layer, or coating over the surface, thereby providing increased friction between skin and implement resulting in better grip.

It is preferred that the composition have a suitably low viscosity that it may be readily converted to an atomized spray, but that the viscosity not be too low because a viscosity that is too low may result in the composition running off of the treatment surface. In this regard, the composition preferably has a viscosity of from about 1 to about 1000 centipoise. The composition may comprise a liquid, a combination of liquids or a combination of one or more liquids and one or more solids that features a suitable viscosity. While a variety of additional ingredients may be included in an inventive composition, as discussed more fully below, an important ingredient in an inventive composition is a fluid base material.

The term "fluid base material" is used herein to refer to a fluid into which additional ingredients may be mixed, dissolved and/or suspended. The fluid base material selected is preferably a propellant. Excellent propellants that may be used are chlorofluorohydrocarbons, butanes, propanes, carbon dioxide, nitrous oxide, nitrogen, dimethyl ether, liquefied petroleum gas, heptane, and isopropanol or mixtures thereof.

The term "silicone oil" is used herein to refer to a liquid silicone composition. Excellent silicone oils that may be used, for example, are cyclomethicone, dimethicone and derivatives thereof. Cyclomethicone is a volatile compound, and is advantageously included in certain inventive compositions because it evaporates when applied to the skin's surface, making the coating more dry to the touch. Other volatile compounds may also be used in this way, including, for example, an organic solvent such as isododecane. Such compounds are particularly useful in embodiments of the invention that utilize an aerosol dispenser as the delivery mechanism, as described in more detail below, because the volatile compounds may be used as liquid solvents in the container that evaporate when dispensed from the container to leave a drier coating on the skin surface.

The fluid base material may alternatively be water, an oil-in-water emulsion or a water-in-oil emulsion. Inventive compositions including water or an emulsion as the base material are often considered to be more elegant because such compositions have a less greasy feel. Such compositions are also typically less expensive to make because in most places water is readily available and inexpensive. Additional advantages of having water in an inventive composition are that the presence of water allows the inclusion of additional water-loving ingredients that would not become suitably dissolved or dispersed in an oil-based composition. When water is included in an inventive composition that also comprises one or more oils, it is readily understood that an emulsifying agent will typically be necessary to produce a stable mix of the water and non-aqueous ingredients in the composition. Examples of suitable emulsifiers that may be used include ethanol, cetyl alcohol, stearyl alcohol, cetearyl alcohol and glycerol monolaurate. It is of course not intended that this list be limiting but simply provide examples of emulsifiers that may be used in accordance of the invention. Additional suitable emulsifiers are set forth on pages 90 to 94 of the C.T.F.A. Cosmetic Ingredient Handbook, First Edition, 1988, which is hereby incorporated by reference. Further guidance to the preparation of stable emulsions generally may be found in U.S. Pat. No. 5,417,961 to Nearn et al., which is hereby incorporated herein by reference in its entirety.

In one excellent aspect of the invention, the composition preferably comprises at least about 1 percent solid particulate material by weight and at least about 20 percent by weight of a fluid base material. More preferably, the composition comprises at least about 10 percent solid particulate material by weight and at least about 50 percent by weight of a fluid based material. In this aspect of the invention, the solid particulate material is preferably particulate calcium carbonate mixed with fumed colloidal silica. The calcium solid particulate preferably has an average particle size of from about 0.01 microns to about 100 microns, more preferably from about 0.01 microns to about 55 microns, and most preferably from about 0.01 microns to about 44 microns. The fluid based material is preferably ethanol. This fluid based material is preferable because its rapid evaporation allows for a fast-drying compound that adheres better to the skin and better covers fine crevices leaving a thin, dry, complete antiperspirant layer. The composition may alternatively include colorants to increase visibility of coverage and grip location of implements. Technology testing of the preferred composition has yielded a decrease in moisture on hands of up to 30 percent as compared to past technologies. Furthermore, the preferred composition remained on the skin up to 75 percent longer than previous technologies, and covered the skin surface up to 25 percent better. This increase in efficiency resulted in the composition lasting up to 50 percent longer than the same mass of previous compositions.

Additional ingredients that may optionally be included in an inventive composition are fragrances, preservatives, anti-bacterial agents, anti-fungal agents, emollients, and medicinal additives that can help prevent the formation of blisters, calluses, and cracking skin. In addition, the composition may comprise one or more different solids as an alternative to calcium carbonate or in addition to calcium carbonate, such as, for example, aluminum chlorohydrate, talc, magnesium carbonate, magnesium silicate, aluminum chloride, and rosin. It is of course not intended that this list limit the invention, but simply provide examples of ingredients that might be included in inventive compositions.

Figure 1:
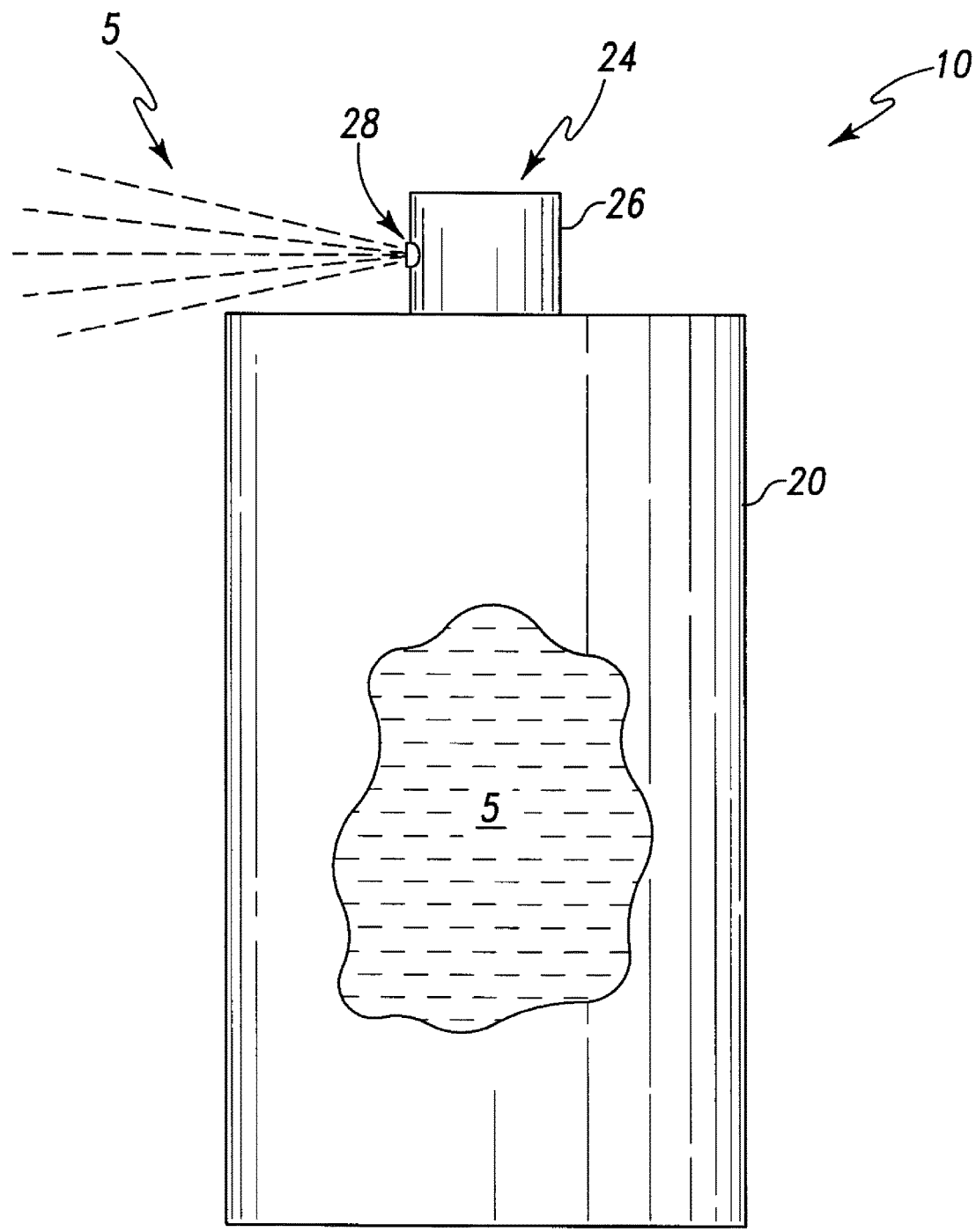
FIG. 1 is a side elevational view, with a cut-out portion, of an atomizing spray dispenser in accordance with one embodiment of the invention.

There are a number of atomizing spray devices that can be used to administer the grip enhancement composition. Referring to FIG. 1, a composition made or selected in accordance with the invention is preferably applied to a skin treatment surface by atomizing the composition 5 and propelling the atomized composition toward the surface using a suitable atomizing spray dispenser 10 comprising a container 20 and an atomizing spray delivery mechanism 24. The atomizing spray delivery mechanism 24 preferably releases the composition 5 from the container 20 through an outlet port 28 when a valve is mechanically actuated. The mechanism 24 preferably features a reciprocating actuator 26.

Figure 2:
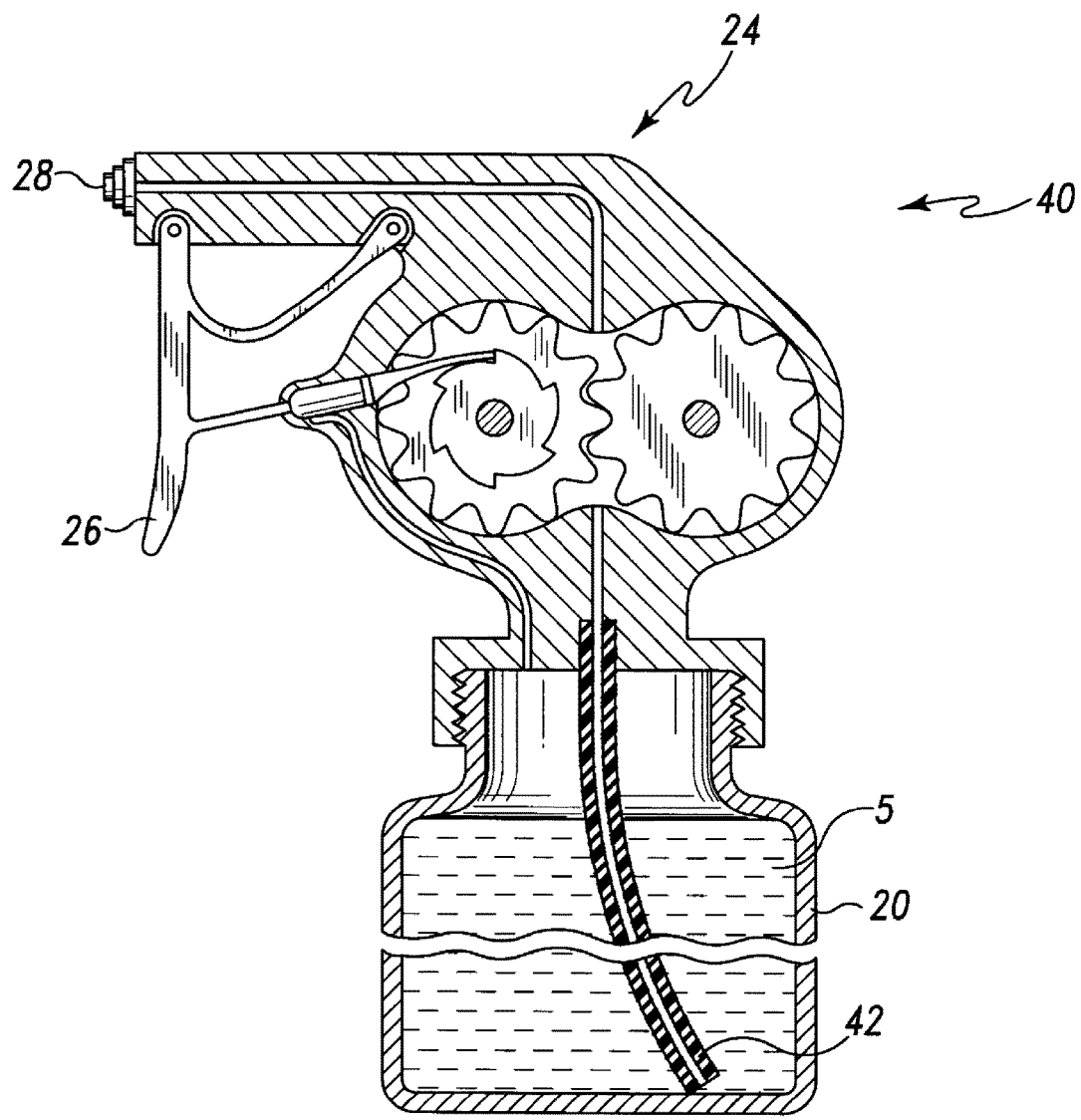
FIG. 2 is a sectional side elevational view of a representative atomizing pump spray dispenser in accordance with another embodiment of the invention.

An excellent atomizing spray delivery mechanism that may be used in accordance with the invention is an atomizing pump spray dispenser 40, a representative example of which is depicted in FIG. 2. As used herein, the term "atomizing pump spray dispenser" is intended to refer to a device that, upon activation of a mechanical pump, such as gear pump 43 of FIG. 2, draws a composition 5 from a container 20, atomizes the composition, and propels the atomized composition substantially in a predetermined direction. It is understood that the composition 5 drawn from container 20 preferably enters a conduit in fluid communication with the pump and having an inlet port 42 positioned near the bottom of container 20. "Atomizing" a composition refers to the separation of the composition into relatively small unitary masses (i.e., typically on the order of about 1 to about 100 microns).

It is important to recognize that the term "pump dispenser" has been used in the prior art to refer to devices for drawing a cream, lotion or ointment from a container and propelling a stream of the cream, lotion or ointment, such as, into the palm of ones hand. This type of dispenser is distinguished from an "atomizing pump spray dispenser" as described herein, because a pump dispenser for propelling a stream of a cream, lotion or ointment is incapable of atomizing the cream, lotion or ointment into an atomized mist or spray. It is understood that the unitary masses, when propelled from an atomizing pump spray dispenser, form a mist or a spray. When the atomized composition is directed toward a given surface at a suitable velocity, the unitary masses adhere to the surface to provide a thin coating of the composition on the surface.

A wide variety of atomizing pump spray dispensers are commercially available, as are a wide variety of designs for actuating the dispensers and for atomizing the composition. While it is not intended that the invention be limited by the design of the atomizing pump spray dispensers, representative examples are set forth in U.S. Pat. No. 5,639,025 to Bush, U.S. Pat. No. 5,881,925 to Ando and U.S. Pat. No. 5,249,747 to Hanson et al.

Another excellent atomizing spray dispenser that may be used in accordance with the invention is a pressure release device. As used herein, the term "pressure release device" is intended to refer to a device that contains a composition under pressure, and, when actuated, opens a valve to release the composition from the pressurized compartment, atomizes the composition, and propels the atomized composition substantially in a predetermined direction by using energy provided by the force of the pressure. The composition may advantageously be maintained under pressure by placing the composition in a pressurized compartment of the container. The composition is releasably contained in the pressurized compartment and when a manually actuating valve is opened, the composition is released from the compartment, atomized, and released from the device as an atomized spray.

Figure 3:
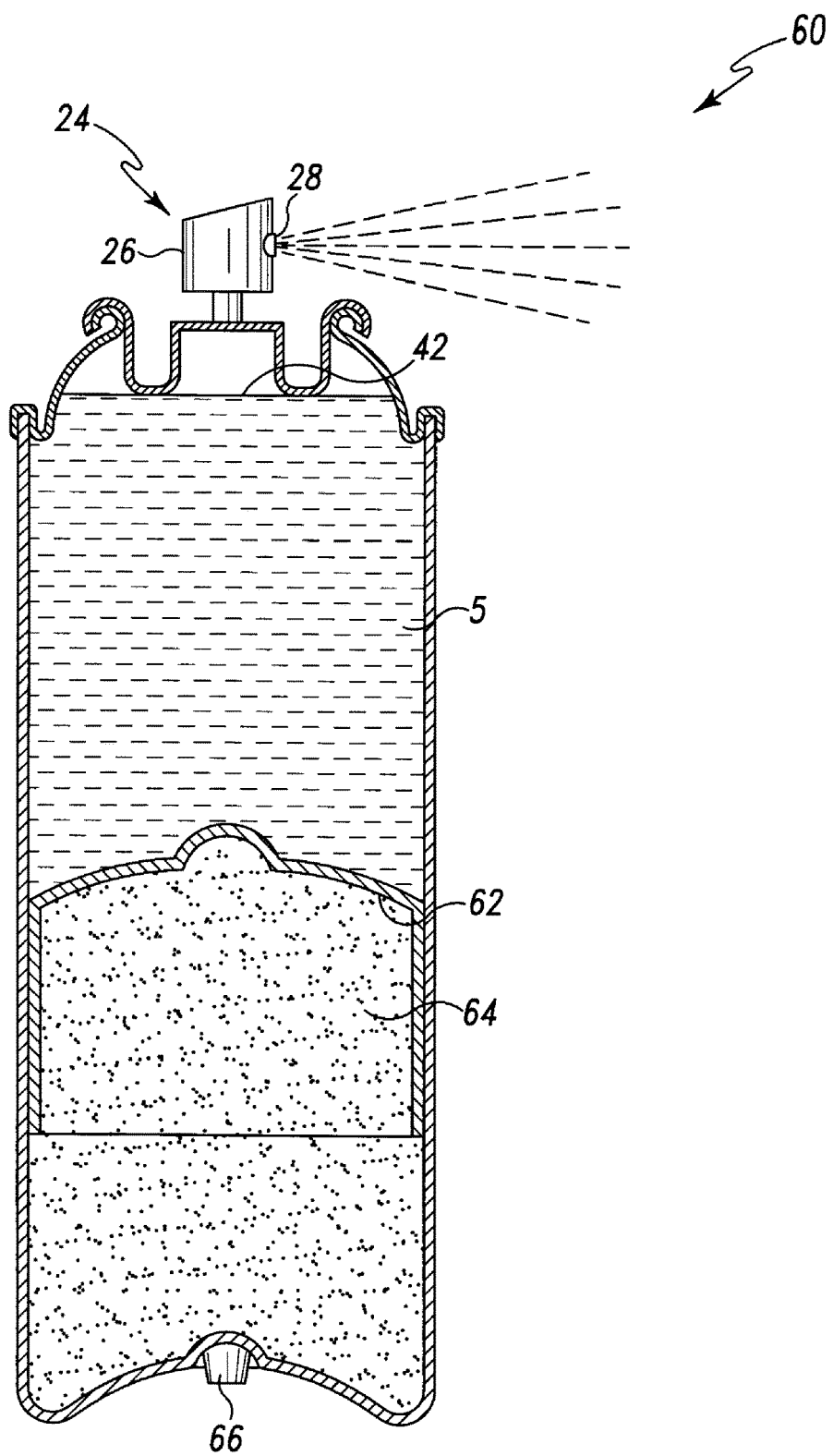
FIG. 3 is a sectional side elevational view of a representative piston-style dispenser in accordance with another embodiment of the invention.

In one excellent embodiment of the invention, a representative example of which is depicted in FIG. 3, the pressure release device is a piston-style dispenser 60, and pressure is maintained on the composition 5 by pressure of a piston 62. The pressure of the piston 62 may be provided by placement of a pressurized gas 64 beneath the piston 62, which placement may be advantageously achieved by introducing gas 64 through a gas charging port 66. Alternatively, pressure on the piston may be achieved by a spring loaded mechanism beneath the piston. Such piston-style dispensers are commercially available, as are a wide variety of designs for actuating the dispensers and for atomizing the composition contained therein. While it is not intended that the invention be limited by the design of the piston-style can, representative examples are set forth in U.S. Pat. No. 4,134,523 to Hansen.

Figure 4:
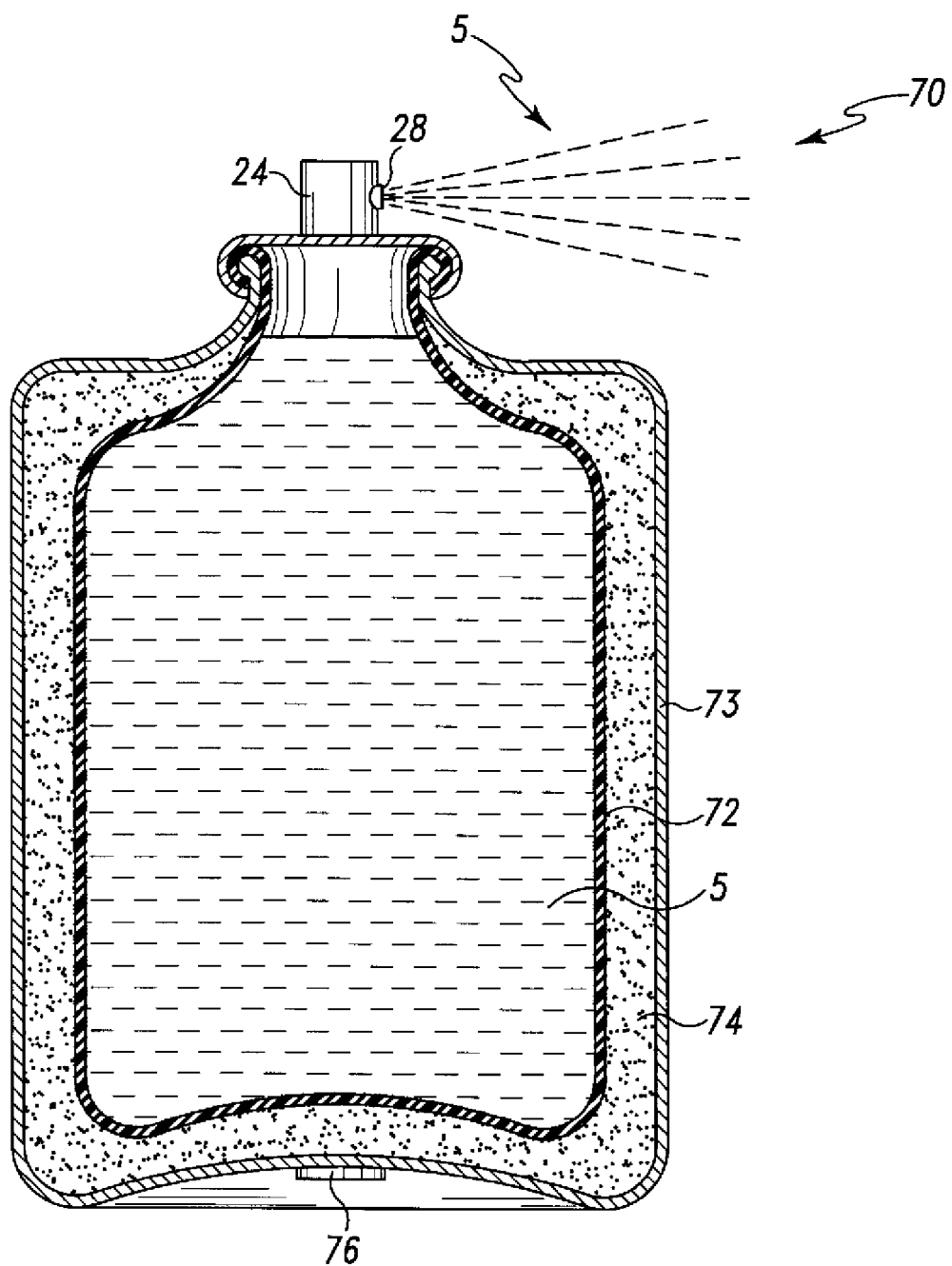
FIG. 4 is a sectional side elevational view of a representative bag-in-can style dispenser in accordance with another embodiment of the invention.
Figure 5:
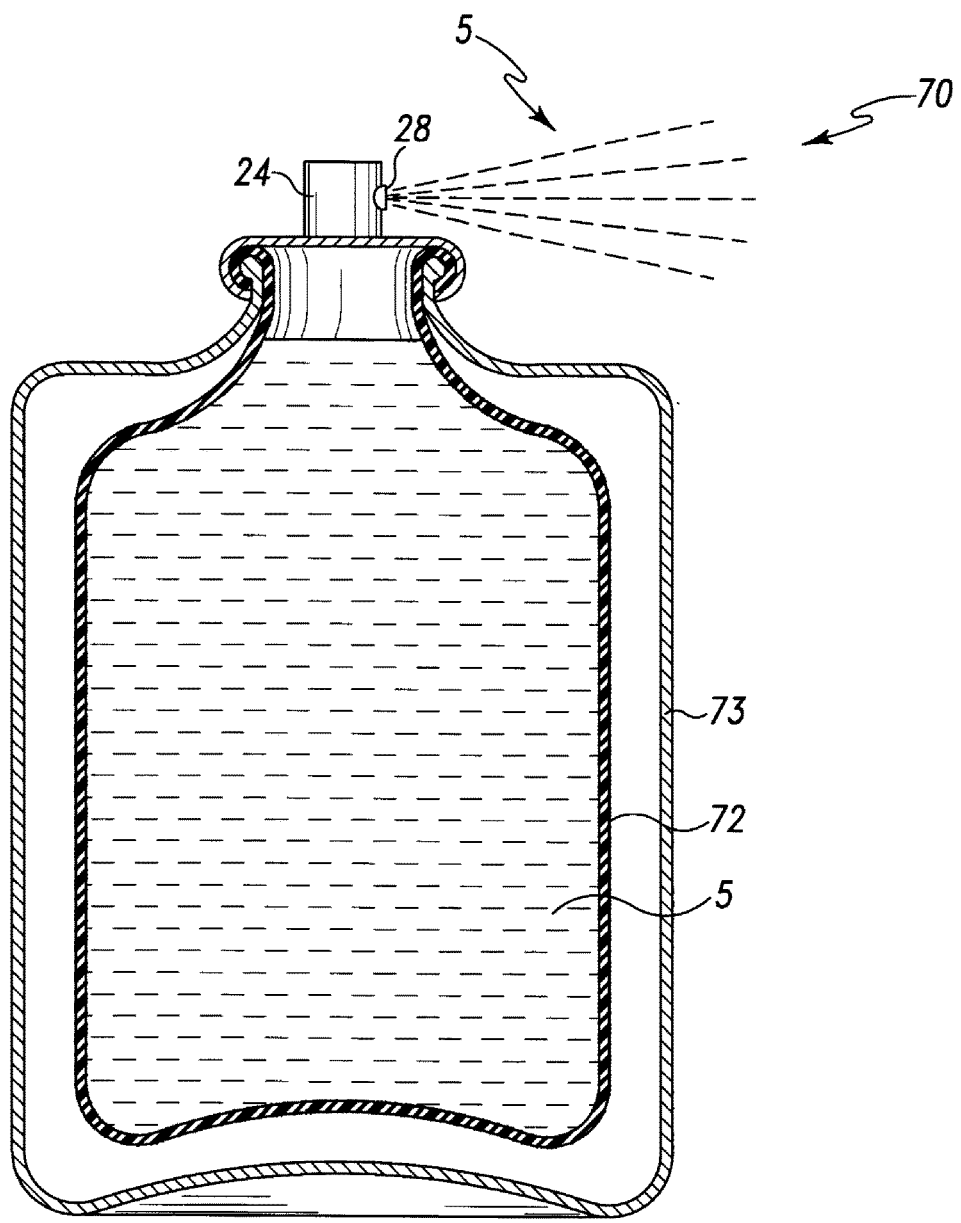
FIG. 5 is a sectional side elevational view of a representative bag-in-can style dispenser in accordance with another embodiment of the invention.

In another excellent embodiment of the invention, representative examples of which are depicted in FIGS. 4 and 5, the pressure release device comprises a bag-in-can-style dispenser 70. The pressurized compartment of such a container is a polymeric bag 72 received inside a rigid can 73. Pressure is maintained on the composition 5 inside the bag 72. In one aspect of the invention, a representative example of which is depicted in FIG. 4, the pressure is maintained upon the composition by a pressurizing gas 74 received in the can 73 and externally to the bag 72. The pressurizing gas 74 may be advantageously placed in the can 73 by introducing gas 74 through a gas charging port 76. In another aspect of the invention, an example of which is depicted in FIG. 5, the bag 72 is an elastic shape-memory bag, and pressure is maintained upon the composition 5 by maintaining the bag in an expanded state. This type of container is commonly referred to as a bladder pack container.

A wide variety of bag-in-can-style containers are commercially available, as are a wide variety of designs for actuating the dispensers and for atomizing the composition contained therein. While it is not intended that the invention be limited by the design of the bag-in-can-style container, representative examples are set forth in U.S. Pat. No. 3,788,521 to Laauwe, U.S. Pat. No. 4,510,734 to Banks et al., and U.S. Pat. No. 5,249,747 to Hanson et al.

Another atomizing spray dispenser that may be used in accordance with the invention, a representative example of which is shown in FIG. 6, is an aerosol device 80. As used herein, the term "aerosol device" is intended to refer to a device that delivers the grip enhancement composition 5 by entraining the same in a carrier stream comprising an inert pressurized propellant gas 82. When such a device is actuated, the composition is released from the container, entrained in a gaseous stream, atomized, and propelled substantially in a predetermined direction by using energy provided by the pressurized gas. It is understood that the composition and carrier gas may alternately be contained in the container in a pre-mixed form, whereby actuation of the device results in a substantially constant release of the mixture. A wide variety of aerosol containers are commercially available, as are a wide variety of designs for actuating the dispensers and for atomizing the compositions contained therein. While it is not intended that the invention be limited by the design of the aerosol container, representative examples are set forth in U.S. Pat. No. 4,001,391 to Feinstone et al., U.S. Pat. No. 4,187,985 to Goth, U.S. Pat. No. 4,239,407 to Knight, U.S. Pat. No. 4,495,168 to Schmolka, U.S. Pat. No. 5,788,389 to de Laforcade, and U.S. Pat. No. RE030,093 to Burger.

While a wide variety of configurations and styles of atomizing spray dispensers are known in the art, the known prior art does not disclose or suggest the present invention, in which excellent grip enhancement compositions are delivered to a skin surface, or sports implement from an atomizing spray dispenser. In view of the above, an excellent system that may be used to dispense grip enhancement compositions is depicted in FIG. 6 and includes a composition as described herein and an atomizing spray dispenser 80 for atomizing the composition and delivering the atomized composition to skin or implement area. The dispenser 80 preferably a container equipped with a spray delivery mechanism 24 configured to atomize and propel the composition 5 toward a treatment surface by entraining the same in a carrier stream comprising an inert pressurized propellant gas 82. The mechanism preferably comprises an inlet port in fluid communication with the interior of the container for receiving the composition, a device for atomizing the composition, and an outlet port 28 for propelling the atomized composition substantially in a predetermined direction. It is readily understood that, in use, the inlet port must be in contact with the composition.

While the invention has been illustrated and described in detail in the drawings and foregoing description, the same is to be considered as illustrative and not restrictive in character, it being understood that only the preferred embodiments have been shown and described and that all changes and modifications that come within the spirit of the invention are desired to be protected.

The invention claimed is:

1. A method for enhancing grip, comprising:
   providing a grip enhancement system comprising an atomizing spray dispenser and an antiperspirant grip composition; wherein the dispenser comprises a container and an atomizing spray delivery mechanism affixed to the container; and wherein the composition is positioned in the container;
   selecting a skin treatment area normally used for gripping; and
   passing the composition through the mechanism to atomize the composition and to propel the atomized composition toward the skin treatment area;
   wherein the composition comprises at least 1 percent by weight of a solid material selected from the group consisting of particulate calcium carbonate, particulate magnesium carbonate and mixtures thereof, and at least 20 percent by weight of a fluid based material selected from the group consisting of monohydric alcohols, polyhydric alcohols, unsaturated aliphatic alcohols, and mixtures thereof.

2. The method according to claim 1, wherein the solid material comprises particulate calcium carbonate.

3. The method according to claim 2, wherein the particulate calcium carbonate has an average particle size of from about 0.01 microns to about 500 microns.

4. The method according to claim 2, wherein the particulate calcium carbonate has an average particle size of from about 0.01 microns to about 100 microns.

5. The method according to claim 2, wherein the particulate calcium carbonate has an average particle size of from about 0.01 microns to about 10 microns.

6. The method according to claim 2, wherein the particulate calcium carbonate has an average particle size of from about 0.01 microns to about 1 micron.

7. The method according to claim 1, wherein the fluid base material is selected from the group consisting of methanol, ethanol, isopropyl alcohol, butanol, pentanol, and cetyl alcohol.

8. The method according to claim 1, wherein the composition further comprises one or more members selected from the group consisting of hydrophilic fumed silica, hydrophobic fumed silica, fumed alumina, colloidal silica, and composite silica.

9. A method for enhancing grip, comprising:
   providing a grip enhancement system comprising an atomizing spray dispenser and an antiperspirant grip composition; wherein the dispenser comprises a container and an atomizing spray delivery mechanism affixed to the container; and wherein the composition is positioned in the container;
   selecting a skin treatment area normally used for gripping; and
   passing the composition through the mechanism to atomize the composition and to propel the atomized composition toward the skin treatment area;
   wherein the composition comprises at least 1 percent by weight particulate calcium carbonate, from 0 percent to about 40 percent by weight fumed silica and at least 20 percent by weight of a fluid based material selected from the group consisting of monohydric alcohols, polyhydric alcohols, unsaturated aliphatic alcohols, and mixtures thereof.

10. A method for enhancing grip, comprising:
    providing a grip enhancement system comprising an atomizing spray dispenser and an antiperspirant grip composition; wherein the dispenser comprises a container and an atomizing spray delivery mechanism affixed to the container; and wherein the composition is positioned in the container;
    selecting a skin treatment area normally used for gripping; and
    passing the composition through the mechanism to atomize the composition and to propel the atomized composition toward the skin treatment area;
    wherein the composition comprises at least 20 percent by weight particulate calcium carbonate, from about 1 percent to about 10 percent by weight fumed silica and at least 20 percent by weight of a fluid based material selected from the group consisting of monohydric alcohols, polyhydric alcohols, unsaturated aliphatic alcohols, and mixtures thereof.

11. The method according to claim 1, wherein the composition further comprises a member selected from the group consisting of talc, clay, kaolin, silica, diatomaceous earth, barium carbonate, magnesium sulfate, barium sulfate, calcium sulfate, aluminum hydroxide, zinc oxide, magnesium hydroxide, calcium oxide, magnesium oxide, titanium oxide, alumina, mica, glass powder, zeolite, silica clay, wood powder, pulp powder, cellulose powder, polytetrafluoroethylene powder, and aromatic polyamide powder.

12. The method according to claim 9, wherein the fluid base material comprises ethanol.

13. The method according to claim 1, wherein the composition further comprises a member selected from the group consisting of fragrances, dyes, medicinal additives, preservatives and mixtures thereof.

14. The method according to claim 1, wherein the solid material comprises particulate magnesium carbonate.

15. The method according to claim 14, wherein the particulate magnesium carbonate has an average particle size of from about 0.01 microns to about 500 microns.

16. The method according to claim 14, wherein the particulate magnesium carbonate has an average particle size of from about 0.01 microns to about 100 microns.

17. The method according to claim 14, wherein the particulate magnesium carbonate has an average particle size of from about 0.01 microns to about 10 microns.

18. The method according to claim 14, wherein the particulate magnesium carbonate has an average particle size of from about 0.01 microns to about 1 micron.

19. The method according to claim 1, wherein the composition further comprises a member selected from the group consisting of fragrances, dyes, antibacterial agents, antifungal agents and mixtures thereof.

* * * * *